United States Patent [19]
Moore et al.

[11] Patent Number: 4,961,416
[45] Date of Patent: Oct. 9, 1990

[54] KNEE BRACE

[75] Inventors: Robert Moore; Steven Lamb, both of Hayward, Calif.

[73] Assignee: Orthopedic Systems, Inc., Hayward, Calif.

[21] Appl. No.: 364,156

[22] Filed: Jun. 12, 1989

[51] Int. Cl.[5] .............................................. H61F 3/00
[52] U.S. Cl. .................................. 128/80 C; 128/80 F
[58] Field of Search ..................... 128/80 C, 80 F, 88, 128/165, 166

[56] References Cited

U.S. PATENT DOCUMENTS

| | | | |
|---|---|---|---|
| 1,044,542 | 11/1912 | Lazzara | 128/80 F |
| 1,847,823 | 3/1932 | Dresser | 128/88 |
| 2,573,866 | 11/1951 | Murphy | 120/80 F |
| 2,690,176 | 9/1954 | Nelson | 128/80 F |
| 2,877,033 | 3/1959 | Koetke | 128/80 F |
| 3,015,825 | 1/1962 | Blatchford | 128/80 F |
| 3,043,297 | 7/1962 | Curmin | 128/80 F |
| 3,172,127 | 3/1965 | Tolotti | 128/80 F |
| 3,194,233 | 7/1965 | Peckram | 128/80 C |
| 3,901,223 | 8/1975 | May | 128/80 F |
| 4,508,111 | 4/1985 | Hepburn | 128/88 |
| 4,523,585 | 6/1985 | Lamb et al. | 128/88 |
| 4,565,190 | 1/1986 | Pirmantgen et al. | 128/88 |
| 4,712,542 | 12/1987 | Daniel et al. | |
| 4,801,138 | 11/1989 | Airy et al. | 128/80 C |

FOREIGN PATENT DOCUMENTS

| | | | |
|---|---|---|---|
| 1430990 | 4/1976 | United Kingdom | 128/80 F |
| 1449554 | 9/1976 | United Kingdom | 128/80 F |

OTHER PUBLICATIONS

The 4-Point Knee Brace- Donjoy Taking the Initiative in Orthopedics-not dated or numbered pages.

*Primary Examiner*—Richard J. Apley
*Assistant Examiner*—Rachel Healey
*Attorney, Agent, or Firm*—Bielen, Peterson & Lampe

[57] ABSTRACT

A leg brace usable after knee ligament surgery utilizing first and second members which are held to the femoral and tibial portions of the leg. A hinge mechanism is also included in the brace for permitting pivotal rotation between the first and second members with the bending or flexion of the knee. A bar is extended across a selected portion of the leg. The bar is biased against the leg by a spring to prevent translation between the tibia and femoral for a particular angular range of extension of the knee portion of the leg.

11 Claims, 3 Drawing Sheets

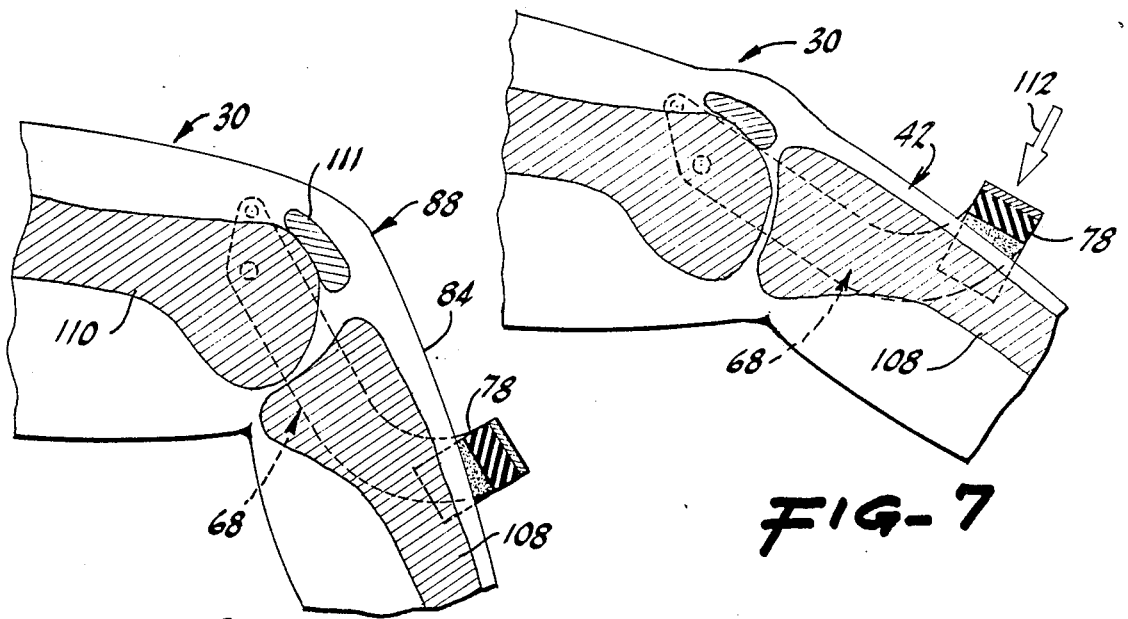
FIG-6
FIG-7
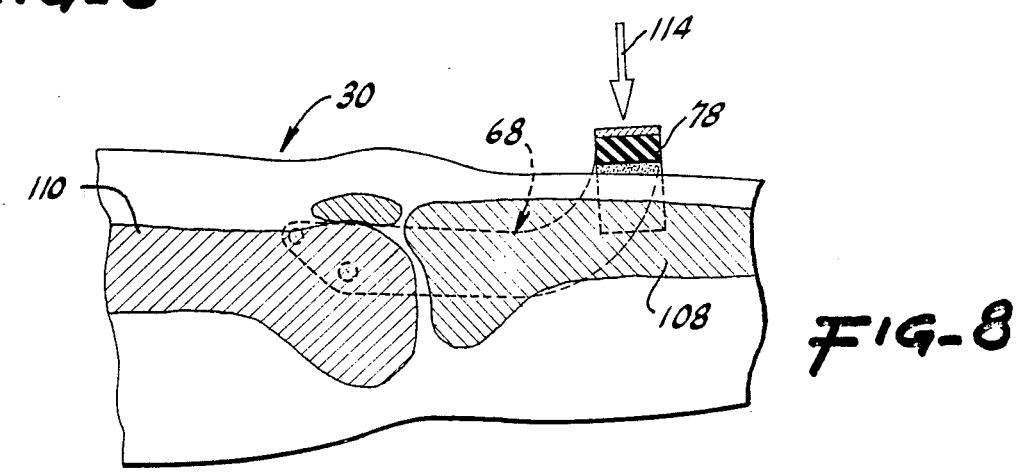
FIG-8
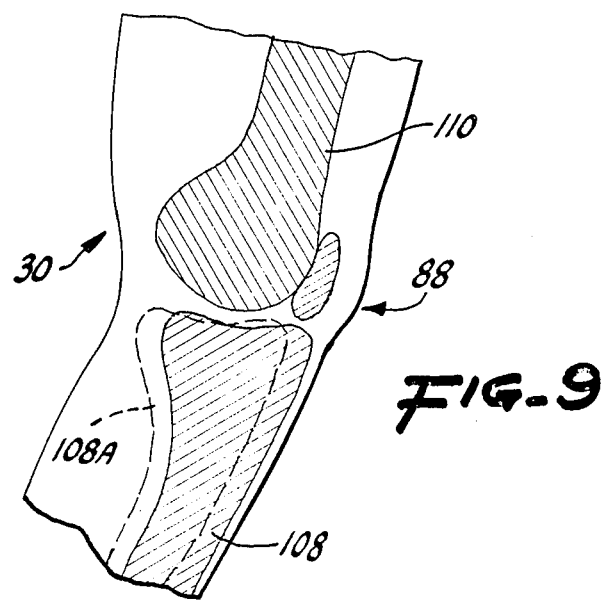
FIG-9

KNEE BRACE

BACKGROUND OF THE INVENTION

The present invention relates to a novel brace for the knee portion of the leg which is particularly useful for patients recovering from ligament surgery.

It has been accepted in the medical field that use of a hinged knee brace is the best system to support a knee after ligament surgery. U.S. Pat. No. 4,523,585 discloses a novel hinge mechanism for such type of knee brace.

Anterior and posterior crucial ligaments (ACL and PCL) are often damaged during vigorous activities, such as sports. The most common ligament repair involves the ACL. This surgery involves the grafting or fixing of natural ligaments in place of the damaged ACL by an elaborate drilling and locating procedure. U.S. Pat. No. 4,712,542 describes such a ligament repair procedure.

It has been recognized that the rotation of the tibial and femoral portions of the leg about the knee is a very complex motion. Essentially, the knee involves a multiple axis rotation and translation. The latter motion has also been referred to as "drawer". Unfortunately, translation or drawer between the femoral and tibial portions of the leg tends to damage a freshly repaired ACL or PCL. It has been discovered anterior drawer or translation occurs in the human knee when the knee is extended between about 30° of flexion and full extension (0° of flexion). In other words, little or no translation takes place between full flexion of the knee (90°) and flexion to 30°.

Although this problem has been recognized in the medical profession, solutions proposed to remedy the same have been less than satisfactory. For example, some prior art devices employ an elastic strap connected to uprights on the cuffs or elements which span the hinge mechanisms. Such elastic straps merely stiffen the connection of the cuff to the leg without preventing translation between the tibial and femoral leg portions on either side of the knee joint.

A knee brace which selectively prevents translation of the tibia and femur while permitting rotation therebetween would be a great advance in the medical field.

SUMMARY OF THE INVENTION

In accordance with the present invention a novel and useful knee brace for use after ligament surgery is provided.

The brace of the present invention utilizes a first member and a second member each including means for holding the same to the femoral and tibial portion of the leg on either side of the knee joint, respectively. Each member includes a band extending across the leg with an adjustable strap for completing encompassment of the leg. Stays or stiffeners may be included in such members. The brace of the present invention is also provided with hinge means for permitting pivotal rotation of the first member relative to the second member. Such hinge means is linked to the first and second members to form a unit. The hinge may be of a known construction and include stop means for limiting the degree of rotation of the knee.

A bar is also included in the present invention and is intended for being forced against the tibia. The bar includes a pad having spaced contact points to obviate damage to the patella, which generally has been intentionally damaged to obtain grafting material for the repair of the ACL or PCL.

Spring means is also envisioned in the present invention to bias the bar against the tibial portion of the leg only during a selected portion of the flexion range of the knee. As heretofore stated, a desirable flexion range would be between 30° and full extension of the knee (0° of flexion). The spring means may include a coil spring confined to a cylinder which exerts a force on a rod. The rod would be pivotally attached to the bar which is itself pivotally attached to the hinge means.

It may be apparent that a novel and useful knee brace usable after ligament surgery is provided.

It is therefore and object of the present invention to provide a knee brace which is capable of preventing translation or drawer during a selected portion of the flexion range of the knee.

It is another object of the present invention to provide a leg brace which prevents further damage to the ACL or PCL in patients who have undergone such ligament repair prior to the healing of the ligaments.

Another object of the present invention is to provide a knee brace which permits full rotation of the knee without translation at certain portions of the flexion range of the knee.

Yet another object of the present invention is to provide a knee brace which provides stability of early ambulation of patients undergoing ligament repair surgery.

A further object of the present invention is to provide a leg brace for post ligament surgery which prevents translation between the femur and tibia and subsequent damage to the freshly repaired ligament, yet does not agitate or injure the patellar region of the knee.

The invention possesses other objects and advantages especially as concerns particular features and characteristics thereof which will become apparent as the specification continues.

BRIEF DESCRIPTION OF THE DRAWINGS

FIG. 6 is a sectional schematic view of the action of the brace bar of the present invention on leg bones where the knee joint has been flexed about 60°.

FIG. 7 is a sectional schematic view of the action of the brace bar of the present invention on a knee which has been flexed 30°.

FIG. 8 is a sectional schematic view of the brace bar of the present invention on leg bones where the knee joint has been fully extended.

FIG. 9 is a sectional schematic view of a knee joint which has been extended to within 20° of full extension (20° of flexion) depicting schematically the actual position of the femoral and tibial bones of the leg at a knee joint, compared to the supposed position of a tibial bone, braced with the present invention, shown in phantom.

Figure 1:
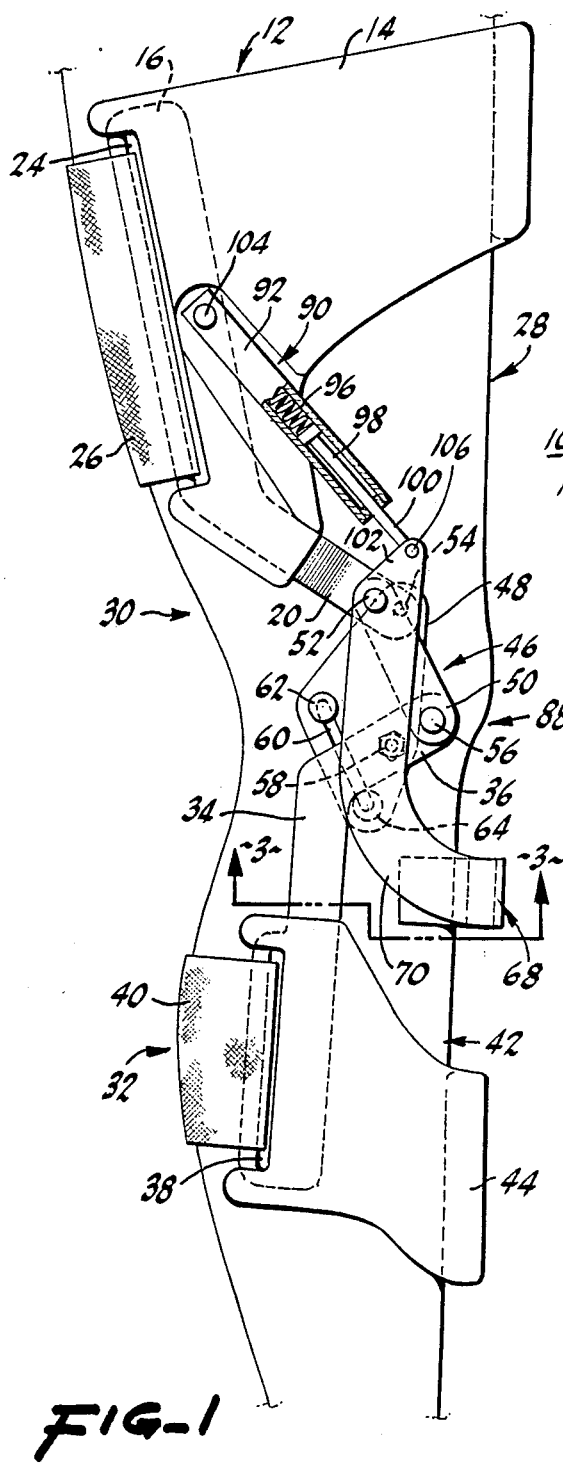
FIG. 1 is a side elevational view of the brace of the present invention shown on a human leg fully extended.

For a better understanding of the invention reference is made to the following detailed description of the preferred embodiments which should be referenced to the hereinabove described drawings.

DESCRIPTION OF THE PREFERRED EMBODIMENTS

Various aspects of the present invention will evolve from the following detailed description of the preferred embodiments which should be referenced to the prior described drawings.

The invention as a whole is shown in the drawings by reference character 10. The leg or knee brace 10 includes as one of its elements a first member 12. First member 12 possesses a cuff 14 which is generally constructed of soft foam material. Cuff 14 is fixed to a pair of relatively rigid stays 16 and 18 which terminate in exposed angular arms 20 and 22, FIGS. 1 and 2. Stays 16 and 18 are formed with an eye such as eye 24 of stay 16 to form an anchor point 24 for adjustable strap 26. First member 12 is intended to encompass or fit around the femoral portion 28 of leg 30.

Second member 32 also includes a stay 34 having an angular arm 36. Again, stay 34 provides an eye 38 which serves as an anchor point for adjustable strap 40 which is intended to wrap about the tibial portion 42. In this regard, cuff 44 formed of soft foam-light material holds stay 34 in place around tibial portion 42 of leg 30. These surfaces of cuffs 14 and 44 which engage leg 30 possess a degree of friction prevents the distal sliding of brace 10, thus, maintaining the position shown on FIGS. 1 and 2.

Angular arms 20 and 36 stays 16 and 34, respectively, serve as the primary links for hinge means 46, which has been thoroughly described in the U.S. Pat. No. 4,523,585 column 2 lines 46-68, column 3 lines 1-68, and column 4 lines 1-36. These portions of the cited patent are incorporated by reference herein. Hinge 46 also includes cross links 48 and 50. Pivot pins 52, 54, 56, and 58 constitute the four pivot points of hinge means 46. Slot 60 includes slide stops 62 and 64. Hinge means 46 connects arm 20 of stay 18 at pivot pin 52. Likewise, arm 36 of stay 34 connects to hinge means 46 at pivot pin 56. Thus, hinge means 46 permits pivotal rotation of first member 12 relative to second member 32. Hinge means 66 associated with stay 18 is essentially identical to hinge means 44 and will not be further described herein.

Figure 2:
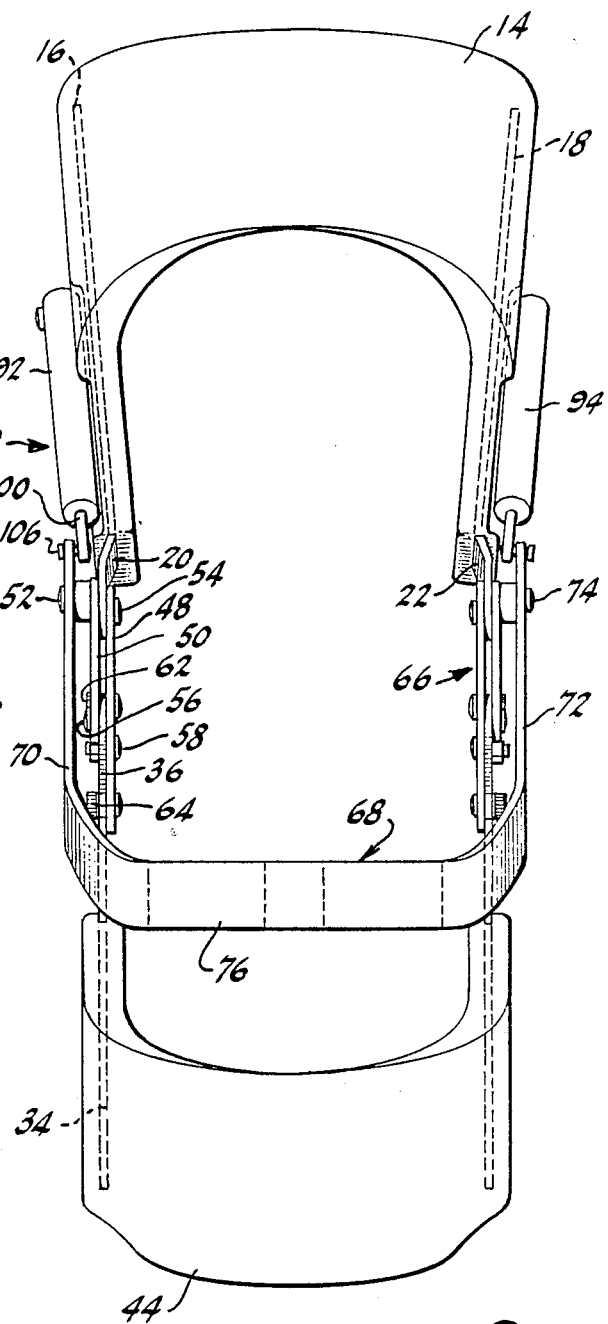
FIG. 2 is a front elevational view of the brace of the present invention.
Figure 3:
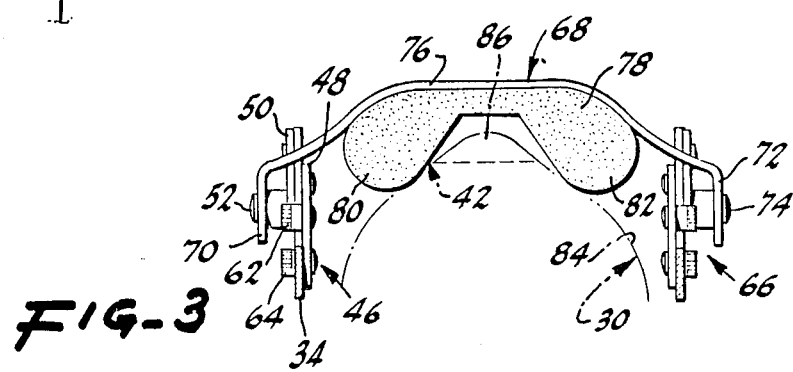
FIG. 3 is a sectional view taken along line 3—3 of FIG. 1 emphasizing the pad portion of the bar mechanism.

With reference to FIGS. 1-3, it may be observed that brace 10 also includes a bar or bridging member 68 which is depicted as extending across tibial portion 42 of leg 30. Bar 68 may be constructed of rigid or flexible material. Bar 68 includes legs 70 and 72 which connect to pivot pins 52 and 74 of hinge means 46 and 66, respectively. Link 76 of bar 68 extends across tibial portion 42 of leg 30. Pad 78 possesses a pair of protuberances or bulges 80 and 82 between hiatus 81 which touch skin surface 84 on either side of patellar region 86 of leg 30. Such a structure for pad 78 avoids irritation of patellar region 86 which normally has been employed as the source of the ligament graft used in repairing the crucial ligaments within knee 88. Pad 78 contacts surface 84 of leg 30 during flexion and extension of leg 30, as will discussed in greater detail as the specification continues.

Brace 10 is also constructed with spring means 90 which biases bar 78 against skin surface 84 of leg 30. Spring means 90 is depicted in FIG. 2 as including a pair of spring cylinder units 92 and 94 which are pivotally linked to stays 16 and 18 respectively. Since the spring unit 92 associated with stay 16 is essentially identified to the spring cylinder unit 94 associated with stay 18, only the former will be described in detail. A coil spring 96 is found within spring cylinder 92 unit. Plunger 98 includes a rod 100 which pivotally attaches to ear 102 of leg 70 extending from link 76 of bar 68. Pivot pin 104 and pivot pin 106 serve as connection elements for spring cylinder unit 90 between stay 16 and ear 102 of par 68.

Figure 4:
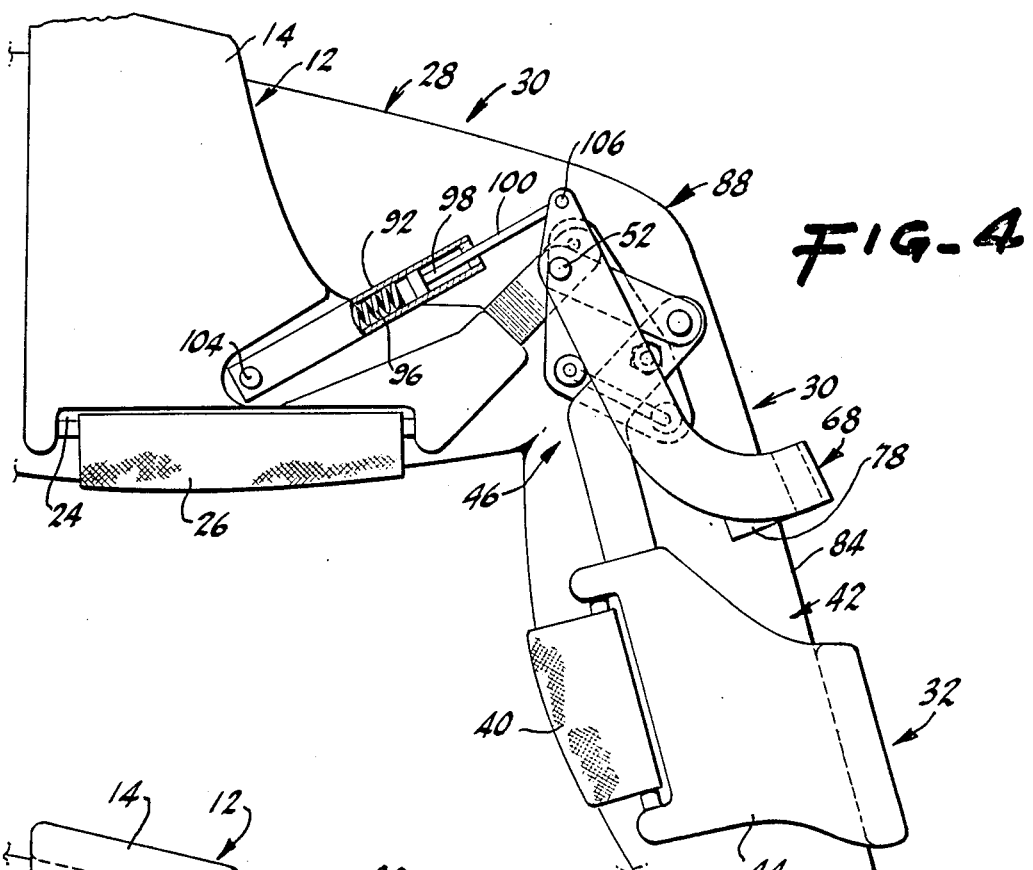
FIG. 4 is a side elevational view of the brace of the present invention in place on an almost fully flexed knee.
Figure 5:
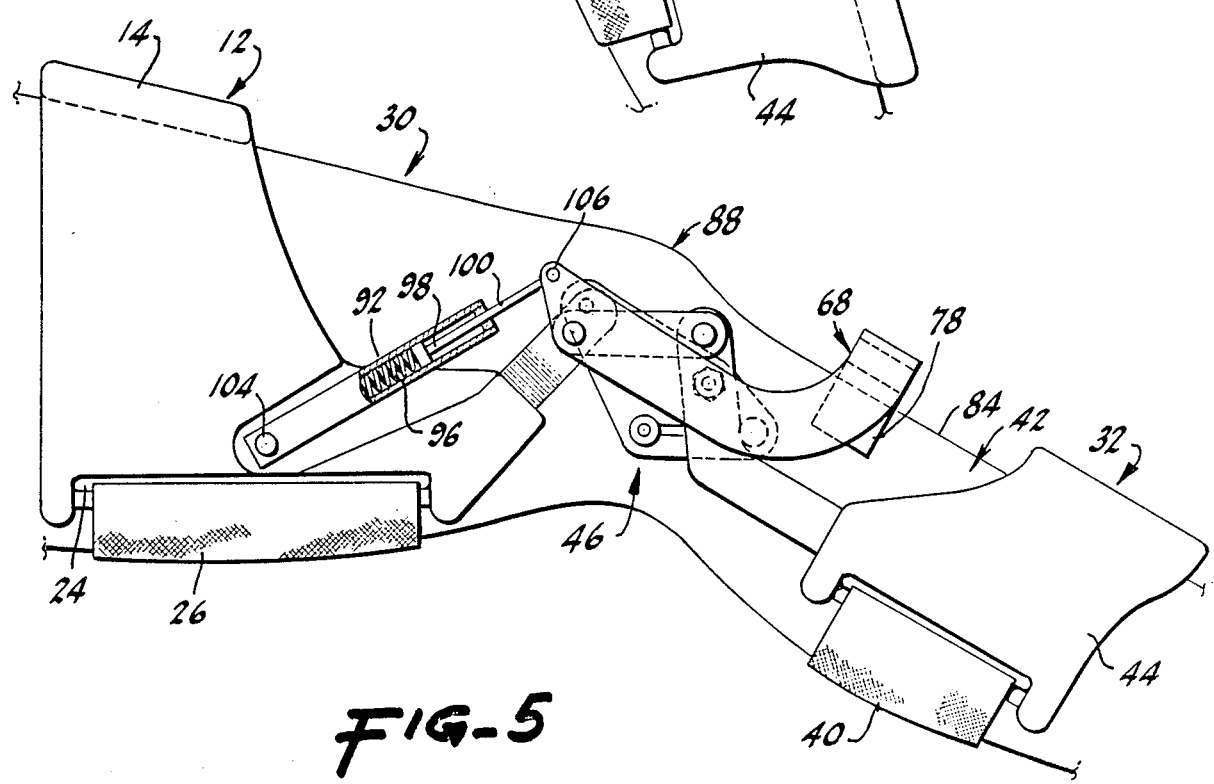
FIG. 5 is a side elevational view of the brace of the present invention in place on a knee which has been flexed only about 30°.

In operation, FIGS. 4 and 5 depict the motion of the relative components of brace 10. In FIG. 4, knee 88 of leg 30 has been flexed to approximately 90°. It should be noted that although pad 78 of bar 68 touches surface 84 of leg 30 in the tibial portion 42, essentially no restraining force is applied to leg 30. This should be apparent from the fact that plunger 98 within cylinder unit 92 does not contact coil spring 96. However with reference to FIG. 5, when the leg 30 knee portion 88 is flexed about 30° (extended 60°) a force is applied to the tibial portion 42 of leg 30 by bar 68 and pad 78. Again, this occurs since plunger 98 ls now contacting coil spring 96 within spring cylinder unit 92. Of course, the angle of flexion associated with the initiation of the force of bar 68 on the tibial portion 42 of leg 30 may be adjusted according to the determination of the relative distances between coil spring 96 and plunger 98 within cylinder 92. Also, the force of spring 96 may be varied to provide the proper force of bar 68 on tibial portion 42 of leg 30. Further, bar 68 may be constructed to pull the tibial portion 42 of leg 38 instead of the pressing engagement shown in the embodiment depicted in the drawings. Moreover, force may be applied to the femoral region 28 of leg 30 to achieve the same results i.e. prevention of drawer or translation of the tibial portion 42 of leg 30 relative to the femoral portion 28 of leg 30. Such movement is illustrated in FIGS. 6-9. FIG. 6 depicts leg 30 where the knee portion 88, thereof, has been flexed approximately 60°. Pad 78 is tin contact with skin surface 84 but does not exert any essential force on tibia 108 to provide translation restraint relative to femur 110. It should be noted that the drawings also show patella 112. Turning to FIG. 7, it may be observed that leg 30 is depicted having approximately 25° of flexion. Spring means 90 is now acting on the tibia 108 via tibial portion 42 of leg 30. Directional arrow 112 depicts such force. With respect to FIG. 8, leg 30 is depicted has having full extension (0° flexion). At this point bar 68 and associated pad 78 exerts maximum force on tibia 108, directional arrow 114. IT should be noted that the amount of force exerted on tibia 108 increases from 30° of flexion to full extension of leg 30 due to the nonlinearity of the force exerted by spring means 90, and in particular, coil spring 92. However, other springs having linear or decreasing forces may also be used if the case warrants. Finally, FIG. 9 depicts a leg having 20° of flexion. Tibia 108 is depicted as being unbraced and is shown as translated toward the front of knee 88. Tibia 108A, depicted in phantom, shows the position of tibia 108 when tibia 108 is held against translation by brace 10. As heretofore noted, it is important to obviate drawer or translation of tibia 108 relative to femur 110 for several months after ligament surgery to prevent damage to the ligament graft during this healing period.

While in the foregoing embodiments of the invention have been set forth in considerable detail for the purpose of making a complete disclosure of the invention, it may be apparent to those of skill in the art that numerous changes may be made in such detail without departing from the spirit and principles of the invention.

What is claimed is:

1. a leg brace usable after ligament surgery on the knee comprising:
    a. a first member including means for holding said first member to the femoral portion of the leg;
    b. a second member including means for holding said second member to the tibial portion of the leg;
    c. hinge means for permitting pivotal rotation of said first member relative to said second member, said hinge means being linked to said first and second members, said first and second members and said hinge means forming a unit;
    d. a bridging member extending across a selected portion of the leg, said bridging member being attached to said unit;
    e. spring means for biasing said bridging member against the selected portion of the leg during a selected one part of the flexion range of the knee to prevent translation between the femoral and tibial portions of the leg, yet permitting pivotal rotation of said unit during another part of the flexion range of the knee.

2. The leg brace of claim 1 in which said spring means further includes means for biasing said bridging member against the tibial portion of the leg during a selected portion of the flexion range the knee.

3. The leg brace of claim 1 in which said bridging member further comprises a pad which contacts the leg.

4. The leg brace of claim 1 in which said bridging member is pivotally attached to said hinge means.

5. The leg brace of claim 4 in which said spring means includes a spring exerting force on a rod, said rod being pivotally attached to said bridging member.

6. The leg brace of claim 1 which further includes means for stopping the pivotal rotation of said first member relative to said second member.

7. The leg brace of claim 1 which said hinge means includes a pair of hinges placed over opposite sides of the knee joint.

8. The leg brace of claim 3 in which said pad includes multiple leg contact points with a hiatus therebetween.

9. The leg brace of claim 5 in which said spring means includes a cylinder confining said spring there within, and said rod connects to a plunger capable of contacting said spring within said cylinder.

10. The leg brace of claim 9 in which said bridging member further comprises a pad which contacts the leg.

11. The leg brace of claim 10 in which said pad includes multiple leg contact points with a hiatus therebetween.

* * * * *